US00PP23173P3

(12) United States Plant Patent
Egger

(10) Patent No.: US PP23,173 P3
(45) Date of Patent: Nov. 6, 2012

(54) ***HEUCHERA* PLANT NAMED 'ROOT BEER'**

(50) Latin Name: ***Heuchera* sp.**
Varietal Denomination: Root Beer

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 113 days.

(21) Appl. No.: 12/932,453

(22) Filed: Feb. 25, 2011

(65) Prior Publication Data

US 2012/0222184 P1 Aug. 30, 2012

(51) Int. Cl.
*A01H 5/00* (2006.01)

(52) U.S. Cl. ..... Plt./440

(58) Field of Classification Search ..... Plt./440
See application file for complete search history.

*Primary Examiner* — June Hwu

(74) *Attorney, Agent, or Firm* — Klarquist Sparkman, LLP

(57) ABSTRACT

A new and distinct *Heuchera* plant characterized by medium red brown leaves year round, very free flowering on medium to short flower stalks, creamy yellow flowers on red peduncles, well branched, mounding habit, and excellent vigor.

1 Drawing Sheet

Botanical denomination: *Heuchera* sp.

Variety designation: 'Root Beer'.

Cross reference to: *Heuchera* 'Cherry Cola' (U.S. Plant Pat. No. 22,967).

BACKGROUND OF THE INVENTION

The present invention relates to a new and distinct cultivar of *Heuchera* and given the cultivar name of 'Root Beer'. *Heuchera* is in the family Saxifragaceae. *Heuchera* 'Root Beer' originated from a cross between *Heuchera* 747-5, a proprietary non-commercial hybrid, as the seed parent, and *Heuchera* 766-5, a proprietary non-commercial hybrid, as, as the pollen parent.

Compared to the seed parent, *Heuchera* 747-5, the new cultivar has smaller leaf size and red brown rather than rose to olive leaf color.

Compared to the pollen parent, *Heuchera* 766-5, the new cultivar has creamy yellow rather than light pink to white flowers and red brown rather than purple black leaves.

Compared to its sibling *Heuchera* 'Cherry Cola', the new cultivar has darker colored leaves and creamy yellow rather red than flowers.

This new *Heuchera* is uniquely distinguished by:

1. medium red brown leaves year round,
2. very free flowering on medium to short flower stalks,
3. creamy yellow flowers on red peduncles,
4. well branched, mounding habit, and
5. excellent vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

The photograph shows a 1-year-old plant of *Heuchera* 'Root Beer' growing in the ground in full sun in the trial field in August in Canby, Oreg.

DETAILED PLANT DESCRIPTION

The following is a detailed description of the new *Heuchera* cultivar based on observations taken in April of 2-year-old specimens growing in the ground in the garden in full sun in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, $5^{th}$ edition.

Plant:

*Form*.—Basal rosette, herbaceous perennial.
*Hardiness*.—USDA Zone 4 to 9.
*Size*.—15 cm tall from top of the foliage to the ground and 35 cm wide.
*Habit*.—Mounding.
*Vigor*.—Excellent.

Leaf:

*Type*.—Simple.
*Arrangement*.—Rosette.
*Shape*.—Broadly ovate to orbicular.
*Lobing/division*.—5 to 7 shallow lobes, shallow secondary lobes.
*Venation*.—Palmate.
*Margins*.—Broadly crenate.
*Apex*.—Mucronulate.
*Base*.—Cordate, lobes usually overlapping at the base.
*Blade size*.—Grows to 8.5 cm long and 9.3 cm wide.
*Texture*.—Leathery.

*Surface texture*.—Pubescent on top side, glandular on bottom.

*Petiole description*.—Grows to 15 cm long and 2.5 mm wide, glandular hairs, Red Purple 59B.

*Leaf color*.—Topside, spring leaves are Greyed Purple 185A, bottom side Red Purple 59B; summer leaves topside Greyed Purple N186C with slight white veiling, White N155B; bottom side Red Purple 59B; winter leaves topside are Greyed Purple 183A with tints of Brown 200C, bottom side Red Purple 59B.

Inflorescence:

*Size*.—Grows to 7 cm wide and 31 cm long.

*Type*.—Thyrse.

*Number of flowers per thyrse*.—About 70.

*Number of thyrse*.—About 20 in the first spring flush.

*Peduncle*.—Grows to 30 cm long, 4 mm wide at base, Greyed Purple 187B, glandular hairs, with 1 to 3 pedicellate cauline leaves (grow to 6 cm long and 6 mm wide, ovate to orbicular, 3 to 5 lobed, margins crenate, tip mucronulate, base cordate, glandular, topside Greyed Red 181B, bottom side Greyed Purple 185A).

*Pedicel*.—Variable in size, with glandular hairs, Greyed Purple 187B.

*Bloom period*.—April through June in Canby, Oreg.

Flower bud:

*Size*.—2.5 mm wide and 4 mm long.

*Description*.—Glandular puberulent, ovoid, down facing.

*Color*.—Bottom half Greyed Purple 185B, top half Greyed Yellow 161B tinted Greyed Purple 185B.

Flower:

*Type*.—Perfect.

*Shape*.—Campanulate.

*Size*.—6 mm long and 4 mm wide.

*Corolla description*.—5 petals, 3 mm long and 1 mm wide, spatulate with 0 to 2 jagged side lobes, margins entire, tip acute, sparsely glandular on both sides, White NN155C.

*Calyx description*.—Campanulate, 5 mm long and 4 mm wide, with 5 lobes divided ½ way to the base, each 1.7 mm wide and 2.5 mm long, glandular hairs outside and inside, tips obtuse, margin entire; color outside on bottom half Greyed Yellow 161A and on top half Greyed Yellow 161B with tips tinted Greyed Purple 185B, inside color Greyed Yellow 161C.

*Stamen description*.—5 in number, 1 mm long, no pollen, male sterile.

*Pistil description*.—1, 2-beaked, 2 mm long and 1.5 mm wide; Greyed Yellow 160C overall.

*Fragrance*.—None.

*Lastingness*.—Each thyrse blooms for about 3 weeks on the plant.

Fruit:

*Type*.—Two-beaked ovoid capsule.

*Fertility*.—Low.

*Color*.—Greyed Brown 199C.

Seed:

*Shape*.—Linear.

*Size*.—2 mm long.

*Color*.—Black 202A.

Pest and disease tolerance: Excellent disease resistance to powdery mildew, the common problem of *Heuchera*. Susceptible to *Heuchera* rust and root weevils.

I claim:

1. A new and distinct *Heuchera* plant as herein illustrated and described.

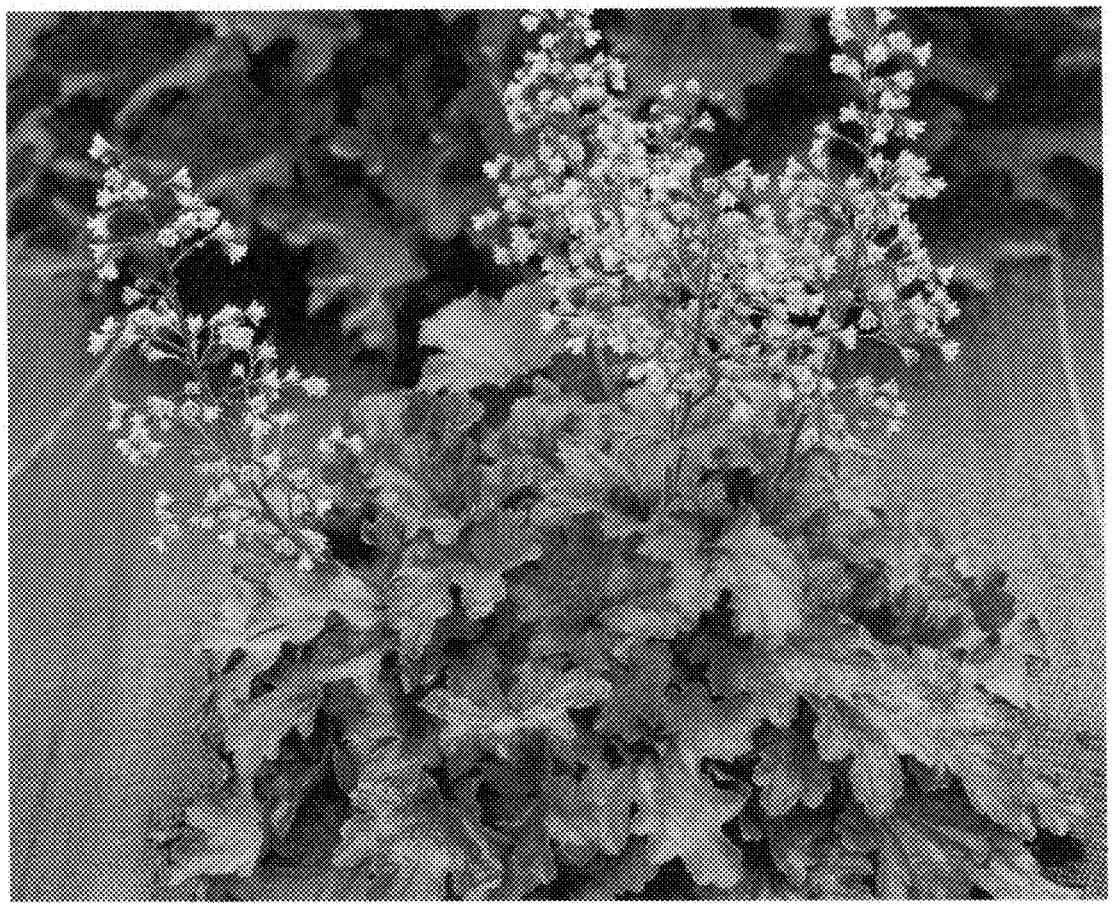

* * * * *